(12) United States Patent
Groeschner

(10) Patent No.: US 6,860,632 B2
(45) Date of Patent: Mar. 1, 2005

(54) INSTRUMENT MATERIAL HOLDER AND METHOD OF FABRICATION THEREOF

(75) Inventor: Donald L. Groeschner, New Milford, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 0 days.

(21) Appl. No.: 10/628,537

(22) Filed: Jul. 28, 2003

(65) Prior Publication Data

US 2005/0025217 A1 Feb. 3, 2005

(51) Int. Cl.[7] .......................... G01N 25/20; G01K 17/00
(52) U.S. Cl. ............................ 374/12; 374/14; 374/33; 422/102; 436/147; 73/864.91
(58) Field of Search ................. 374/10–14, 31–34, 374/43, 208, 29, 30; 422/51, 102; 436/147; 73/864.91

(56) References Cited

U.S. PATENT DOCUMENTS

| | | | | |
|---|---|---|---|---|
| 3,445,630 A | * | 5/1969 | Ulam ........................ 219/438 |
| 3,545,253 A | * | 12/1970 | Iwata et al. ................ 374/13 |
| 3,605,494 A | * | 9/1971 | Progelhof et al. ........... 374/29 |
| 3,732,722 A | | 5/1973 | Norem et al. ................ 374/12 |
| 4,178,800 A | * | 12/1979 | Thomann .................... 374/33 |
| 4,330,933 A | | 5/1982 | Bullinger et al. ............. 29/612 |
| 4,368,991 A | * | 1/1983 | Hentze ....................... 374/12 |
| 4,575,928 A | * | 3/1986 | Starnes ....................... 29/611 |
| 5,098,196 A | | 3/1992 | O'Neill ....................... 374/11 |
| 5,225,766 A | | 7/1993 | O'Neill ....................... 323/280 |
| 5,295,745 A | * | 3/1994 | Cassettari et al. ............ 374/10 |
| 5,439,291 A | | 8/1995 | Reading ....................... 374/11 |
| 6,561,692 B2 | * | 5/2003 | Danley ....................... 374/29 |

FOREIGN PATENT DOCUMENTS

| | | | | |
|---|---|---|---|---|
| JP | | 1263545 | 10/1989 | |
| WO | | WO 9406000 A1 | * 3/1994 | ......... G01N/25/48 |

* cited by examiner

*Primary Examiner*—Diego Gutierrez
*Assistant Examiner*—Stanley J. Pruchnic, Jr.
(74) *Attorney, Agent, or Firm*—St. Onge Steward Johnston & Reens LLC

(57) ABSTRACT

A housing for a material holder includes an intermediate housing member having a generally horizontal member, an upper recess and a lower recess, an upper housing member having a generally horizontal member and a wall defining a material holding chamber, the upper housing member being seated within the upper recess of the intermediate housing member, and a lower housing member having a generally horizontal member, the lower housing member being seated within the lower recess of the intermediate housing member. The upper recess, the generally horizontal member of the intermediate housing member and the generally horizontal member of the upper housing member define a first cavity adapted to receive a first winding assembly, and the lower recess, the generally horizontal member of the intermediate housing member and the generally horizontal member of the lower housing member define a second cavity adapted to receive a second winding assembly.

26 Claims, 7 Drawing Sheets

INSTRUMENT MATERIAL HOLDER AND METHOD OF FABRICATION THEREOF

FIELD OF THE INVENTION

The present invention relates generally to an improved holder for materials used in measuring instruments such as calorimeters and to an improved fabrication method therefor, and more particularly to an improved holder and an improved fabrication method therefor which is particularly suited for use in conjunction with a differential scanning calorimeter.

BACKGROUND OF THE INVENTION

The present invention particularly relates to a material holder used in a differential scanning calorimeter of the type disclosed and claimed in U.S. Pat. No. 3,732,722 ("the '722 patent") for a "Material Holder" issued May 15, 1973 to Norem et al. and assigned to The Perkin-Elmer Corporation of Norwalk, Conn. The entirety of the '722 patent is incorporated by reference herein.

A differential scanning calorimeter is a thermal analytical instrument which operates on the principle that thermal energy is absorbed or evolved during physical or chemical changes in a material which is being analyzed. The differential scanning calorimeter measures the differential energy changes that occur in a sample material as compared to a reference material, during such physical or chemical changes. The sample material and a thermally inert reference material are placed in separate material holders in the same thermal environment and their temperatures are measured during the analysis process.

The material holder, as disclosed in the '722 patent, includes a cylindrical cup having three bottom partitions forming two cavities within the bottom portion of the cup, one of the cavities containing a heating winding, and the other cavity containing a heat-sensing winding. A supporting center post is attached to the bottom of the lowermost partition as a support for the material holder.

In order to produce the material holder, a series of substantially identical discs are punched from sheet stock with a punch and die set to form the three partitions. These discs are successively press fitted into a cylindrical housing and electron beam welded at the disc edges to the cylindrical housing. The heater and sensing windings are sandwiched between the successive disc partitions.

Serious problems have been encountered in the above-described assembly and fabrication method in that it has been found to be extremely difficult to maintain tolerances on the disc diameters and the inside diameters of the cylindrical housings with sufficient precision to avoid very high rejection rates in the assembled material cups. The success of the instrument resides in maintaining extreme precision. The precision in measurement is so important that a noble metal such as platinum, paladium, gold, and their alloys are preferably used as the material of the material holder. Preferably, the metal of which the holder is formed is an alloy of 80% platinum and 20% iridium. The noble metals avoid the problems of oxide formation.

The high precision also requires extremely narrow tolerances in the assembled dimensions of the material holders. Thus, in a material holder which is on the order of one-third of an inch in diameter (actually 0.360 inches in one preferred embodiment), the various partitions must be perfectly parallel with one another with a variation out of parallelism not to exceed 0.001 inch. Also, the various partitions must not be distorted in shape, the compartments containing the windings must be absolutely consistent and uniform in size, within the tolerance of plus or minus seven ten thousandths of an inch, and there must be very good conductivity between the edges of the partition discs and the cylindrical housing. In order to accomplish these purposes, the partitions must be press fitted into position within the cylindrical housing with a tight enough fit to precisely maintain the position of each disc during handling after assembly and before electron beam welding. Furthermore, the press fit must be sufficiently tight to promote the production of a good sound electron beam weld between the disc partition and the cylindrical housing in order to provide a consistently high thermal conductivity through the joint formed thereby. On the other hand, the disc must not be press fitted with so much of an interference fit that it results in distortion of the disc.

One of the biggest problems in achieving the satisfactory press fit of the disc partitions into the cylindrical housing apparently arises because of variations in the diameters of the discs produced by the punch and die set. For a particular batch run of approximately 900 discs between sharpenings of the punch and die set, it has been discovered that the disc diameters may vary in a typical range of about $3/10,000$ths of an inch, or more. These variations in disc diameter are believed to be associated with the wear pattern of the punch and die, and also, possibly, these variations may be related to variations in the toughness and thickness of the sheet metal from which the discs are punched.

Another problem in providing the correct press fit arises particularly in connection with the bottommost disc partition to which the support post is welded. It has been discovered that the support post welding causes the disc to which it is welded to shrink somewhat in diameter, that shrinkage being in the order of 4 to 5 ten thousandths of an inch.

Another major problem in producing a satisfactory press fit of the disc partitions has been found to result from the fact that the electron beam welding of the first (uppermost) partition into the cylindrical housing causes the diameter of that housing to shrink slightly, so as to increase the tightness of the cylinder around the edges of subsequently assembled disc partitions. Similarly, the electron beam welding of the second disc partition causes still a further shrinking of the cylindrical housing for the assembly of the third disc partition.

These problems were substantially obviated by U.S. Pat. No. 4,330,933 ("the '933 patent") for a "Fabrication Method For Instrument Material Holder" issued May 25, 1982 to Bullinger et al. and assigned to The Perkin-Elmer Corporation of Norwalk, Conn. The entirety of the '933 patent is incorporated by reference herein.

The '933 patent teaches an improved fabricating method which compensates for at least part of the fluctuations in disc diameters, and which compensates for the shrinkage of the cylindrical housing during electron beam welding of the first disc which includes the steps of sorting the discs according to diameter into at least two sets including a first set and another set having diameters smaller than the discs of the first set. Cylindrical housings are then machined with an inside diameter somewhat smaller than the outside diameters of the discs of the first set to provide a press fit of the discs of the first set within the housings. After press fitting and electron beam welding of a disc from the first set within each cylinder housing, one of the discs from the smaller diameter set is press fitted into the housing, the smaller diameter of the disc compensating for the shrinkage of the cylinder caused by the welding of the first disc.

In another aspect of the invention disclosed in the '933 patent, an improved fabrication method may be provided in which the discs are divided into at least two sets, including a first set and another set of discs which are larger in diameter than the discs of the first set. A batch of cylindrical housings are then machined with an inside diameter to provide a desired press fit of the discs of the first set within the housings. After a disc from the first set is press fitted into a cylindrical housing and welded therein, one of the larger diameter discs, to which a supporting center post has already been welded, is press fitted into the end of the cylindrical housing. The reduction in the diameter of the last mentioned disc caused by the welding of the center post compensates for the larger initial diameter of the disc and the reduction in the diameter of the cylindrical housing caused by the welding of the earlier disc into the housing.

The above mentioned fabrication processes may be combined into a single process in which the initial run of discs is sorted by diameter into a first set, another set of discs having a diameter smaller than the discs of the first set, and still another set of discs having a diameter larger than the discs of the first set, the discs of the first set being used as the first disc partition to be positioned and welded into each cylindrical housing, the inside diameter of which has been machined to provide the appropriate press fit, the smaller diameter discs being used as the second partition to be press fitted and welded into each housing, and the larger diameter discs being the ones to which supporting posts are attached prior to press fitting and welding into the cylindrical housing to provide the third partition.

While the improved fabrication processes disclosed in the '933 patent obviate many of the problems with the processes disclosed in the '722 patent in that the fabrication processes disclosed in the '933 patent avoid the problems arising from variations in the disc diameters as produced by the punch and die, avoid the problem associated with the shrinkage in the diameter of the bottommost disc partition occasioned by the welding of the support post thereto, and avoid the consequences of the problem of the shrinkage of the cylindrical housing resulting from the electron beam welding of earlier assembled disc partitions in order to improve the press fit of subsequently assembled disc partitions, the fabrication processes disclosed in the '933 patent suffer from disadvantages of their own.

More specifically, the processes disclosed in the '933 patent are very labor intensive to ensure proper spacing, requiring the use of precision tooling fixtures and pins. Even when the operator is extremely careful, it difficult to accurately control the spacing of the heater and the sensor, and it is difficult to achieve reproducibility and consistent performance characteristics between material holders. Moreover, the material holders disclosed in the '933 patent are comprised of a relatively high number of parts, and result in a high rate of scrap material (on the order of 40% to 50%) due to the fact that the heater and sensor assemblies are assembled to the center section from each end. Furthermore, using the processes disclosed in the '933 patent, it is difficult to accurately know where to place the weld with the electron beam welder, which can result in sputtered platinum in the open cavities.

What is desired, therefore, is a holder for materials used in measuring instruments and a fabrication method therefor which requires less labor intensive processes than are currently employed, which ensures proper spacing without requiring the use of precision tooling fixtures and pins, which allows for the spacing of the heater and the sensor to be accurately controlled, which facilitates reproducibility and consistent performance characteristics between material holders, which has a reduced number of parts, which has a reduced scrap rate, and which facilitates the accurate placement of the electron beam weld so as to inhibit sputtered platinum in the open cavities.

SUMMARY OF THE INVENTION

Accordingly, it is an object of the present invention to provide a holder for materials used in measuring instruments and a fabrication method therefor which requires less labor intensive processes than are currently employed.

Another object of the present invention is to provide a holder for materials used in measuring instruments and a fabrication method therefor having the above characteristics and which ensures proper spacing without requiring the use of precision tooling fixtures and pins.

A further object of the present invention is to provide a holder for materials used in measuring instruments and a fabrication method therefor having the above characteristics and which allows for the spacing of the heater and the sensor to be accurately controlled.

Still another object of the present invention is to provide a holder for materials used in measuring instruments and a fabrication method therefor having the above characteristics and which facilitates reproducibility and consistent performance characteristics between material holders.

Yet a further object of the present invention is to provide a holder for materials used in measuring instruments and a fabrication method therefor having the above characteristics and which has a reduced number of parts.

Still a further object of the present invention is to provide a holder for materials used in measuring instruments and a fabrication method therefor having the above characteristics and which has a reduced scrap rate.

Yet another object of the present invention is to provide a holder for materials used in measuring instruments and a fabrication method therefor having the above characteristics and which facilitates the accurate placement of the electron beam weld so as to inhibit sputtered platinum in the open cavities.

These and other objects of the present invention are achieved in one embodiment by provision of a holder for materials for use in a measuring instrument. The holder includes an intermediate housing member, an upper housing member and a lower housing member. The intermediate housing member includes a generally horizontal member, an upper wall extending upwardly from an upper surface of the generally horizontal member, and a lower wall extending downwardly from a lower surface of the generally horizontal member. The upper wall defines a first recess adjacent the upper surface having a first diameter and a second recess adjacent the first recess having a second diameter, the second diameter being greater than the first diameter, while the lower wall defines a third recess adjacent the lower surface having a third diameter and a fourth recess adjacent the third recess having a fourth diameter, the fourth diameter being greater than the third diameter. The upper housing member includes a generally horizontal member and a wall extending upwardly from an upper surface of the generally horizontal member, the wall defining a material holding chamber. The upper housing member is seated within the second recess of the intermediate housing member. The lower housing member includes a generally horizontal member, and is seated within the fourth recess of the intermediate housing member. A first winding assembly is disposed within a first cavity defined by the first recess, the generally horizontal member of the intermediate housing member and the generally horizontal member of the upper housing member, and a second winding assembly is disposed within a second cavity defined by the third recess, the generally horizontal member of the intermediate housing member and the generally horizontal member of the lower housing member.

In certain embodiments, the upper housing member has an outer diameter which is generally equal to or slightly larger than the second diameter of the second recess so as to create a frictional fit between the intermediate housing member and the upper housing member. Similarly, in certain embodiments, the lower housing member has an outer diameter which is generally equal to or slightly larger than the fourth diameter of the fourth recess so as to create a frictional fit between the intermediate housing member and the lower housing member.

Preferably, the intermediate housing member and the upper housing member are electron-beam welded together and the intermediate housing member and the lower housing member are electron-beam welded together. In some embodiments, the first winding assembly includes a pair of oppositely arranged lead-out connector ribbons and the upper wall of the intermediate housing member includes a pair of oppositely arranged slots to allow the lead-out connector ribbons to emerge therethrough. Similarly, in some embodiments, the second winding assembly includes a pair of oppositely arranged lead-out connector ribbons and the lower wall of the intermediate housing member includes a pair of oppositely arranged slots to allow the lead-out connector ribbons to emerge therethrough.

In certain embodiments, the second recess of the intermediate housing member has a beveled upper edge so as to facilitate insertion of the upper housing member therein, and/or the fourth recess of the intermediate housing member has a beveled lower edge so as to facilitate insertion of the lower housing member therein. In some embodiments, an inner surface of the wall of the upper housing member includes a shoulder therein which is arranged to receive and support a cover.

Preferably, the upper housing member, the intermediate housing member and the lower housing member are formed from an alloy comprising about 80% platinum and about 20% iridium. In some embodiments, one of the first winding or the second winding comprises a heating winding and the other of the first winding or the second winding comprises a heat-sensing winding. In certain embodiments, the holder also includes a center post and a washer member attached to the lower housing member.

In another respect, the present invention is directed to a housing for a material holder. In these embodiments, the housing includes an intermediate housing member having a generally horizontal member, an upper recess and a lower recess, an upper housing member having a generally horizontal member and a wall defining a material holding chamber, the upper housing member being seated within the upper recess of the intermediate housing member, and a lower housing member having a generally horizontal member, the lower housing member being seated within the lower recess of the intermediate housing member. The upper recess, the generally horizontal member of the intermediate housing member and the generally horizontal member of the upper housing member define a first cavity adapted to receive a first winding assembly, and the lower recess, the generally horizontal member of the intermediate housing member and the generally horizontal member of the lower housing member define a second cavity adapted to receive a second winding assembly.

In certain embodiments, the upper housing member has an outer diameter which is generally equal to or slightly larger than a diameter of a portion of the upper recess so as to create a frictional fit between the intermediate housing member and the upper housing member. Similarly, in some embodiments, the lower housing member has an outer diameter which is generally equal to or slightly larger than a diameter of a portion of the lower recess so as to create a frictional fit between the intermediate housing member and the lower housing member.

Preferably, the intermediate housing member and the upper housing member are electron-beam welded together and the intermediate housing member and the lower housing member are electron-beam welded together. In some embodiments, the upper recess of the intermediate housing member has a beveled upper edge so as to facilitate insertion of the upper housing member therein. Similarly, in some embodiments, the lower recess of the intermediate housing member has a beveled lower edge so as to facilitate insertion of the lower housing member therein.

In certain embodiments, an inner surface of the wall of the upper housing member includes a shoulder therein which is adapted to receive and support a cover. Preferably, the upper housing member, the intermediate housing member and the lower housing member are formed from an alloy comprising about 80% platinum and about 20% iridium.

In yet another respect, the present invention is directed to a holder for materials for use in a measuring instrument. The holder includes a three-piece housing consisting of an upper housing member, an intermediate housing member and a lower housing member, the three-piece housing defining a first cavity and a second cavity. A first winding assembly is disposed within the first cavity and a second winding assembly is disposed within the second cavity.

Preferably, the intermediate housing member and the upper housing member are electron-beam welded together and the intermediate housing member and the lower housing member are electron-beam welded together. It is also preferable that the upper housing member, the intermediate housing member and the lower housing member are formed from an alloy comprising about 80% platinum and about 20% iridium. In certain embodiments, one of the first winding or the second winding comprises a heating winding and the other of the first winding or the second winding comprises a heat-sensing winding. In some embodiments, the holder further includes a center post and a washer member attached to the lower housing member.

In still another respect, the present invention is directed to a method for fabricating a holder for materials for use in a measuring instrument. An intermediate housing member comprising a generally horizontal member, an upper recess and a lower recess is provided. A first winding assembly is disposed within the upper recess, and an upper housing member comprising a generally horizontal member and a wall defining a material holding chamber is seated within the upper recess in order to define, with the upper recess, the generally horizontal member of the intermediate housing member and the generally horizontal member of the upper housing member, a first cavity with the first winding housed therein. A second winding assembly is disposed within the lower recess, and a lower housing member comprising a generally horizontal member is seated within the lower recess in order to define, with the lower recess, the generally horizontal member of the intermediate housing member and the generally horizontal member of the lower housing member, a second cavity with the first winding housed therein.

The method preferably further includes the steps of electron beam welding the intermediate housing member and the upper housing member together and electron beam welding the intermediate housing member and the lower housing member together. In some embodiments, the method further includes the step of creating a bevel in an upper edge of the upper recess of the intermediate housing member has so as to facilitate insertion of the upper housing member therein and/or the step of creating a bevel in a lower edge of the lower recess of the intermediate housing member has so as to facilitate insertion of the lower housing member therein. In some embodiments, the method further includes the step of creating a shoulder in an inner surface of the wall of the upper housing member, which shoulder is adapted to receive and support a cover.

The invention and its particular features and advantages will become more apparent from the following detailed description considered with reference to the accompanying drawings.

DETAILED DESCRIPTION OF AN EMBODIMENT OF THE INVENTION

Figure 1:
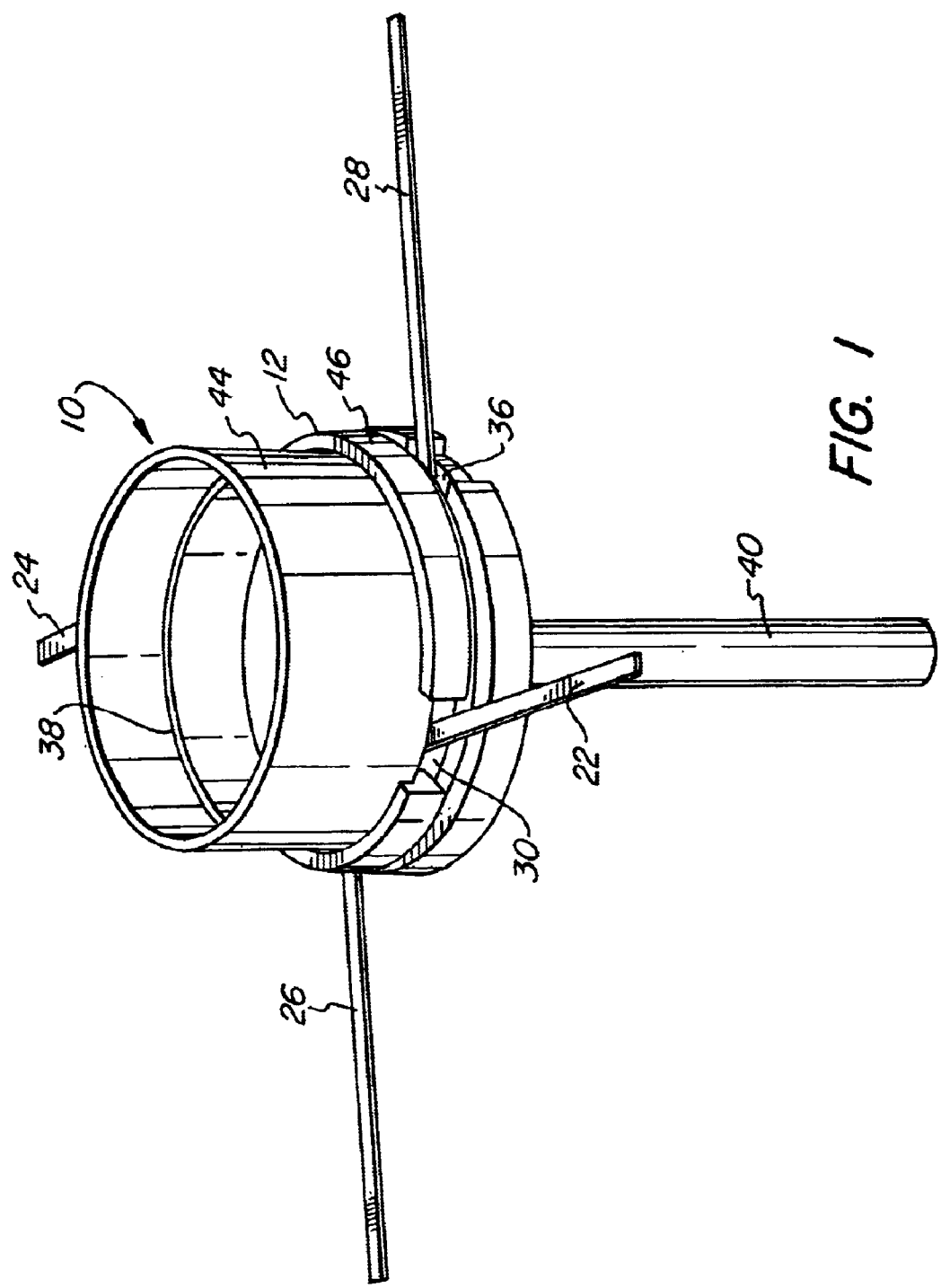
FIG. 1 is a side isometric view of a holder for materials used in measuring instruments in accordance with an embodiment of the present invention.
Figure 2:
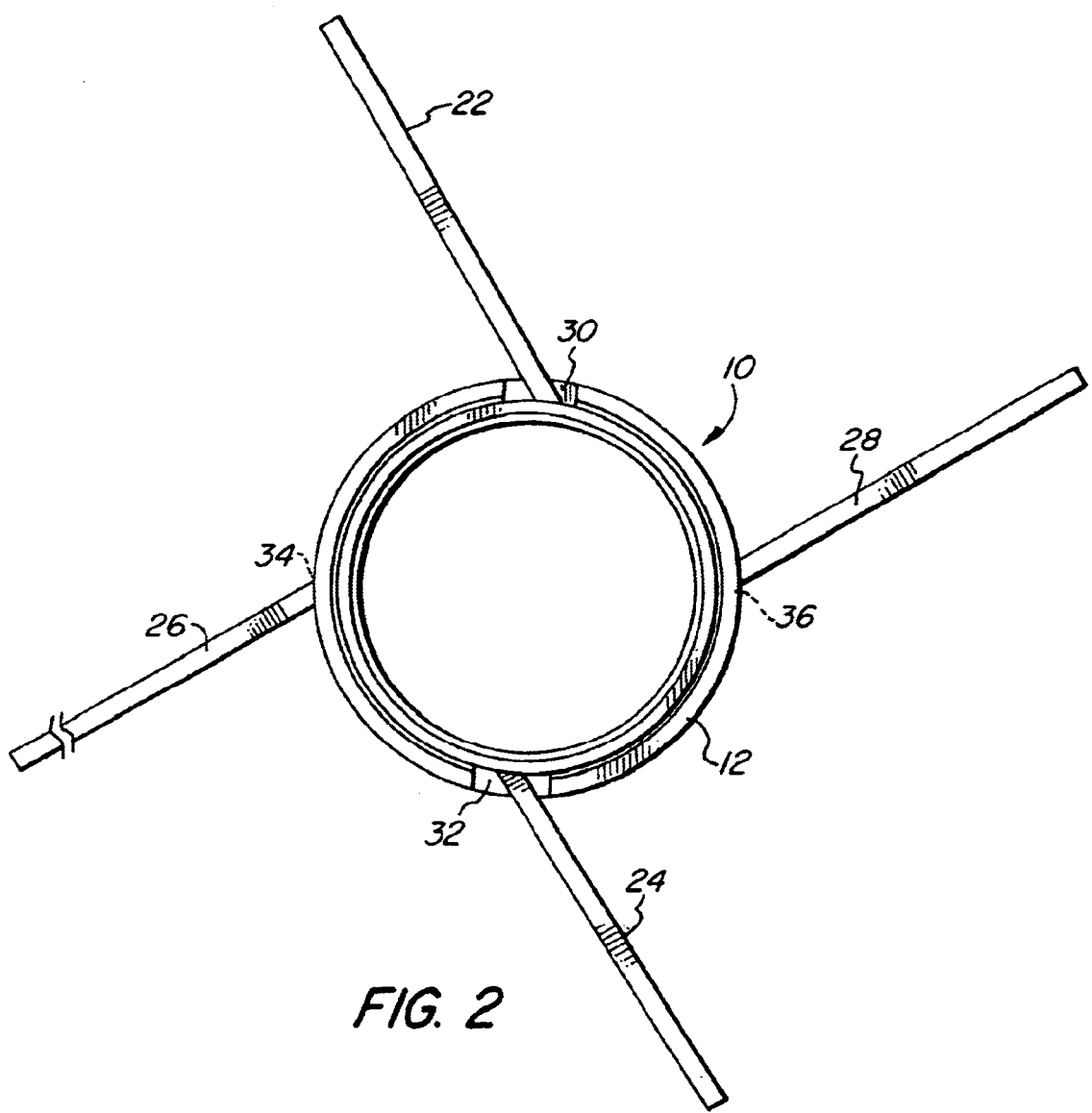
FIG. 2 is a top plan view of the holder for materials used in measuring instruments of FIG. 1.
Figure 3:
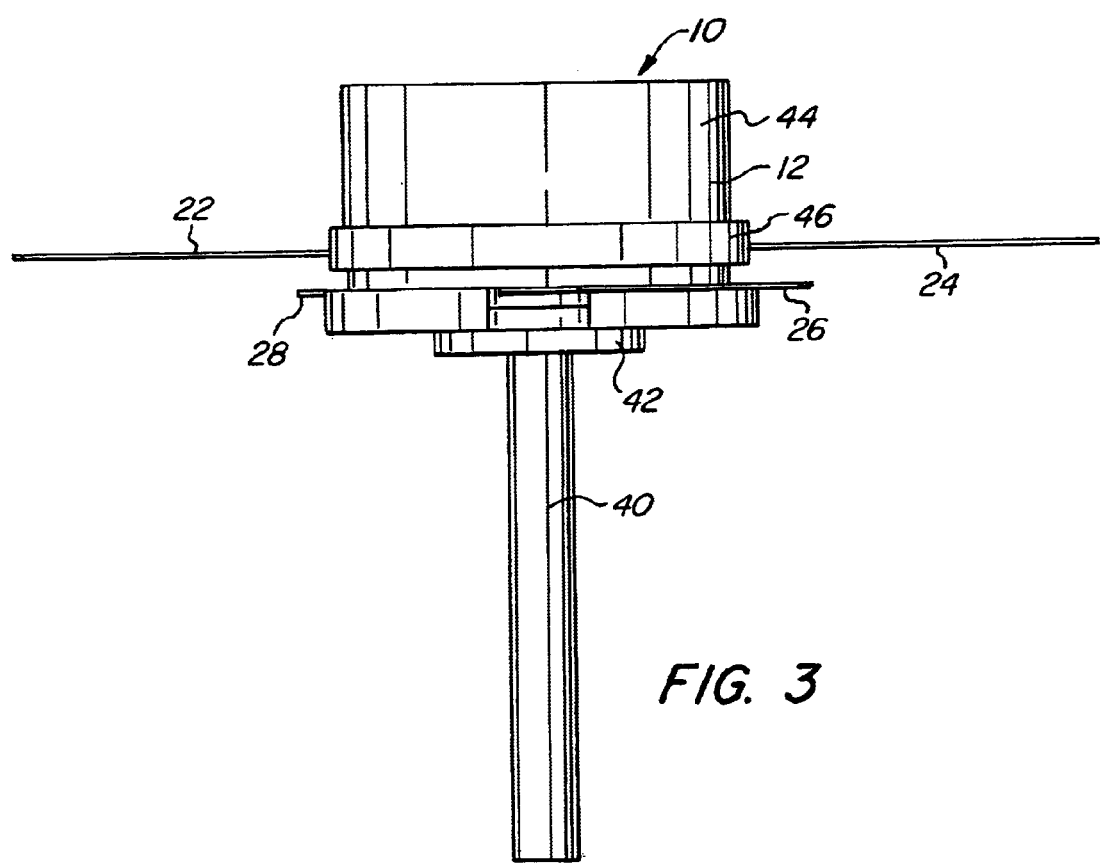
FIG. 3 is a side elevational view of the holder for materials used in measuring instruments of FIG. 1.

Referring first to FIGS. 1 through 4, a material holder 10 used in measuring instruments in accordance with the present invention is shown. The material holder 10 includes a housing 12 which defines a first cavity 14 and a second cavity 16, the configuration of which is described more fully below. Material holder 10 also includes a first winding assembly 18 which is intended to be housed within first cavity 14 within the material holder 10 between adjacent partitions and a second winding assembly 20 which is intended to be housed within second cavity 16 within material holder 10 between adjacent partitions.

Each winding assembly 18, 20 includes a winding holder which preferably consists of a solid aluminum oxide chip upon which a platinum wire winding is wound. A pair of platinum ribbons 22, 24 and 26, 28 are soldered to the ends of the winding of each respective winding assembly 18, 20 and serve as lead-out connectors. The lead-out connector ribbons 22, 24, 26, 28 emerge through oppositely arranged slots 30, 32, 34, 36 in the sides of the housing 12. Each winding assembly 18, 20 is insulated from the adjacent partitions of the assembly by means of insulator discs (not shown), which may include tabs extending through the slots 30, 32, 34, 36 to insulate the lead-out connectors 22, 24, 26, 28. The insulating layers may be formed, for example, of alumina cloth to withstand high temperatures. Winding assemblies 18, 20 may comprise, for example, heater and sensor assemblies.

On the inside surface of the housing 12, in the upper portion thereof, there is a larger diameter portion terminating in a shoulder 38 which is arranged to receive and support a cover (not shown). The material to be tested is supported upon the uppermost partition (more fully described below) and enclosed within material holder 10 by the cover (not shown).

Attached to the bottom of the lowermost partition of housing 12 (more fully described below) is a center post 40. Center post 40 is attached to the lowermost partition by means of a washer member 42. The center post 40 is first electron beam welded to the washer 42, and the washer 42 is electron beam welded to the lowermost partition of housing 12.

Because the structure and function of the components described thus far above in the "Detailed Description of an Embodiment of the Invention" section (in particular the configuration and operation of winding assemblies 18, 20) are well known to those skilled in the art and because further details of these components can be readily found in various prior art references, for example in the '722 patent and the '933 patent (both of which are incorporated by reference herein), a more detailed description of these components is not presented herein. What follows is a detailed description of the novel elements of the present invention.

Figure 4:
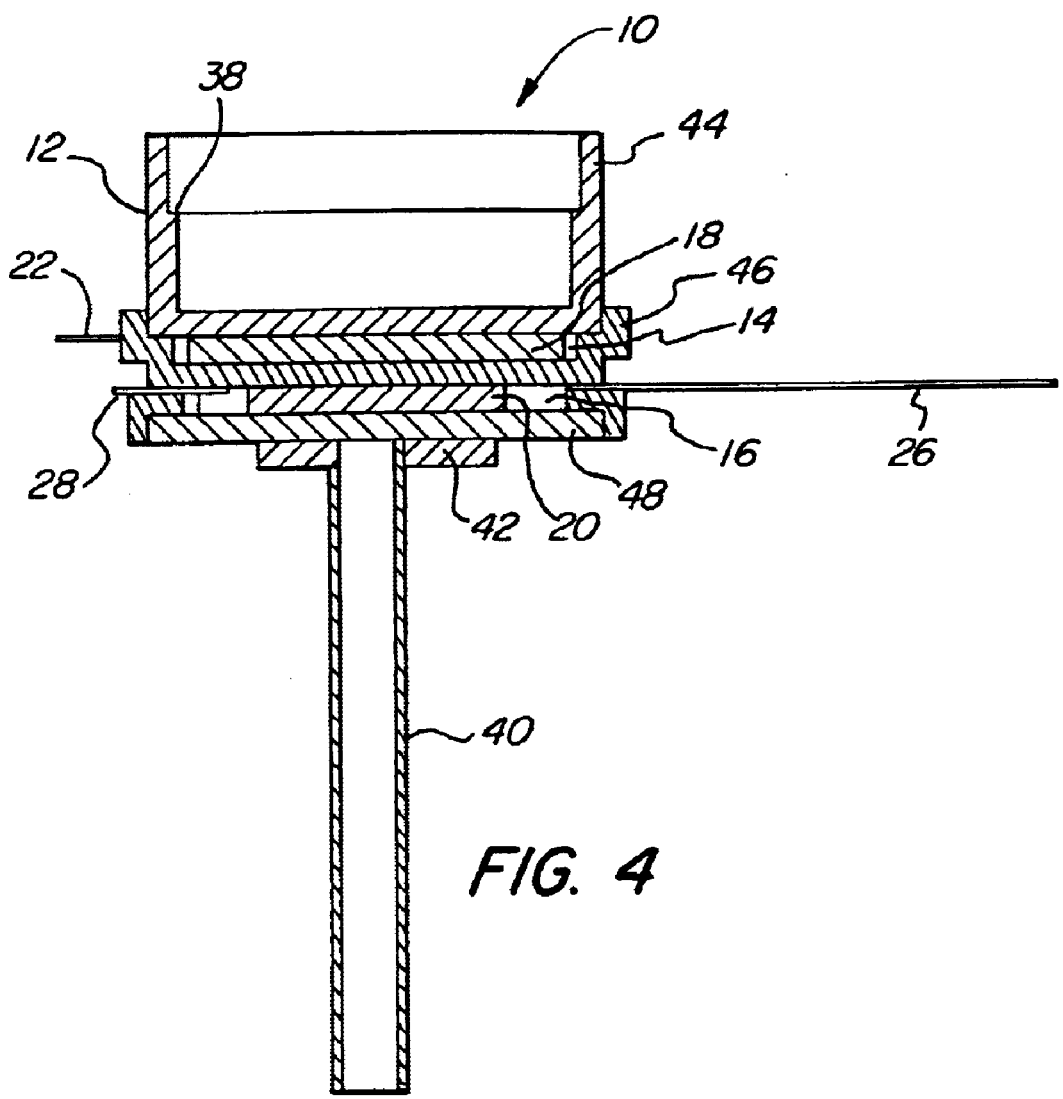
FIG. 4 is a partially cross-sectional side view of the holder for materials used in measuring instruments of FIG. 1.

Rather than the housing being formed from a cylindrical outer housing member and three press-fit discs, housing 12 of the present invention is formed from three components: upper housing member 44, intermediate housing member 46 and lower housing member 48 (the cooperation of which is best seen in FIG. 4). Upper housing member 44, intermediate housing member 46 and lower housing member 48 are preferably formed from a noble metal, such as platinum, paladium, gold, and their alloys. Most preferably, upper housing member 44, intermediate housing member 46 and lower housing member 48 are formed from an alloy of about 80% platinum and about 20% iridium.

Figure 5:
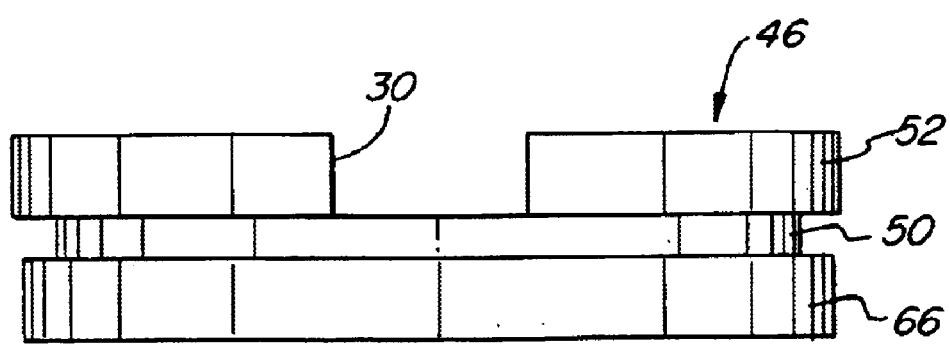
FIG. 5 is a side elevational view of an intermediate housing member of the holder for materials used in measuring instruments of FIG. 1.

Referring now to FIGS. 5 though 7 in addition to FIG. 4, intermediate housing member 46 is shown in more detail. Intermediate housing member 46 includes a generally horizontal member 50 which, when housing 12 is fully assembled as described more fully below, acts as an intermediate partition for housing 12.

Figure 6:
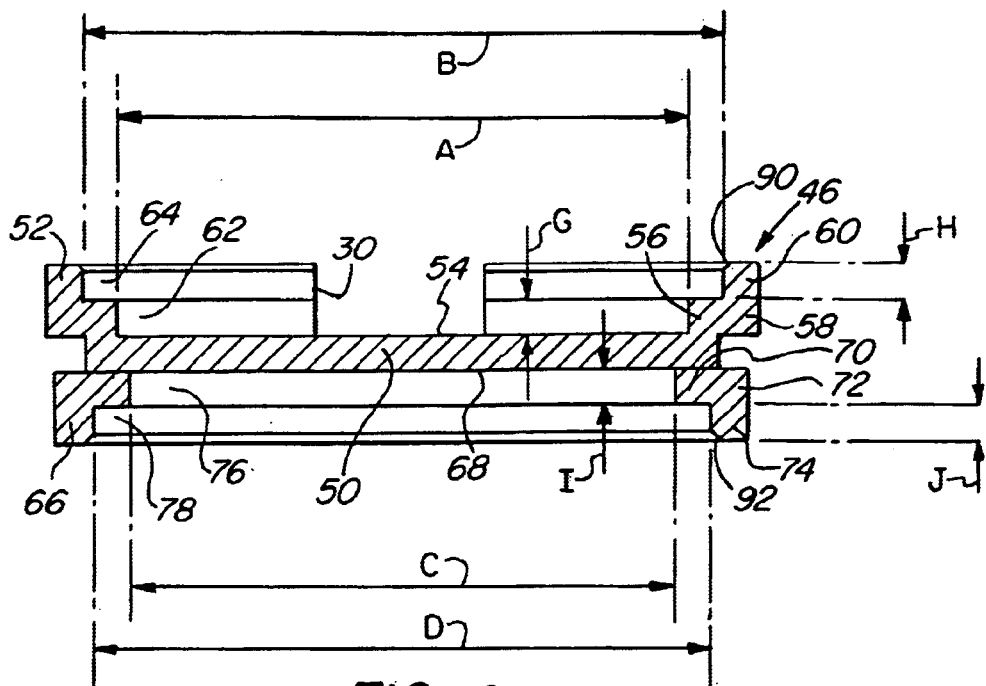
FIG. 6 is a partially cross-sectional side view of the intermediate housing member of FIG. 5.
Figure 7:
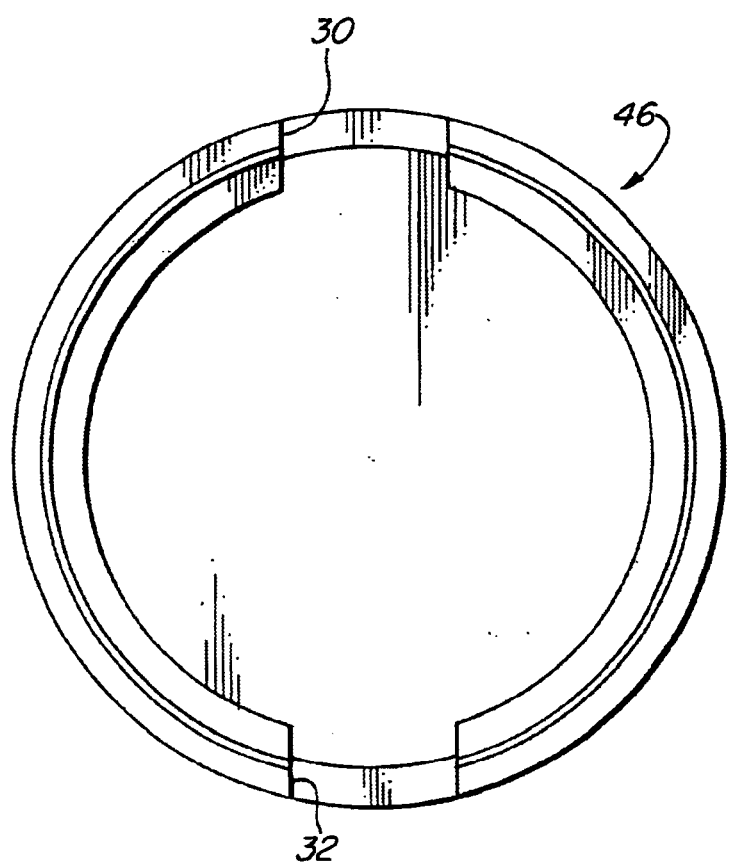
FIG. 7 is a top plan view of the intermediate housing member of FIG. 5.

A wall 52 extends upwardly from an upper surface 54 of horizontal member 50 about a periphery thereof, and defines a first vertical section 56. Wall 52 extends radially outwardly from first vertical section 56 to define a horizontal section 58, and then wall 52 extends upwardly from a periphery of horizontal section 58 to define a second vertical section 60. Thus, as can be best seen in FIG. 6, intermediate housing member 46 includes, on a top surface 54 of horizontal member 50 a wall 52 which defines a first recess 62 adjacent the top surface 54 having a diameter A and a second recess 64 adjacent the first recess 62 having a diameter B, the diameter B of the second recess 64 being greater than the diameter A of the first recess 62. Wall 52 includes a pair of oppositely arranged slots 30, 32 as described above to allow lead-out connector ribbons 22, 24 to emerge from the housing 12 therethrough.

Intermediate housing member 46 also includes a wall 66 extending downwardly from a lower surface 68 of horizontal member 50 about a periphery thereof, which wall 66 defines a first vertical section 70. Wall 66 extends radially outwardly from first vertical section 70 to define a horizontal section 72, and then wall 66 extends downwardly from a periphery of horizontal section 72 to define a second vertical section 74. Thus, as can be best seen in FIG. 6, intermediate housing member 46 includes, on a bottom surface 68 of horizontal member 50 a wall 66 which defines a first recess 76 adjacent the bottom surface 68 having a diameter C and a second recess 78 adjacent the first recess 76 having a diameter D, the diameter D of the second recess 78 being greater than the diameter C of the first recess 76. Wall 66 includes a pair of oppositely arranged slots 34, 36 as described above to allow lead-out connector ribbons 26, 28 to emerge from the housing 12 therethrough.

Figure 8:
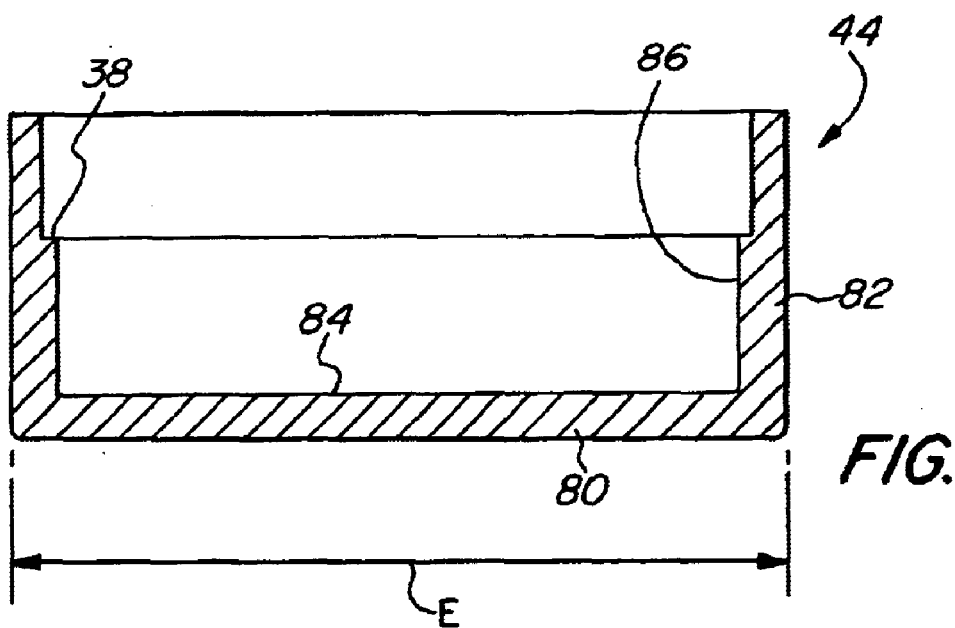
FIG. 8 is a partially cross-sectional side view of an upper housing member of the holder for materials used in measuring instruments of FIG. 1.
Figure 9:
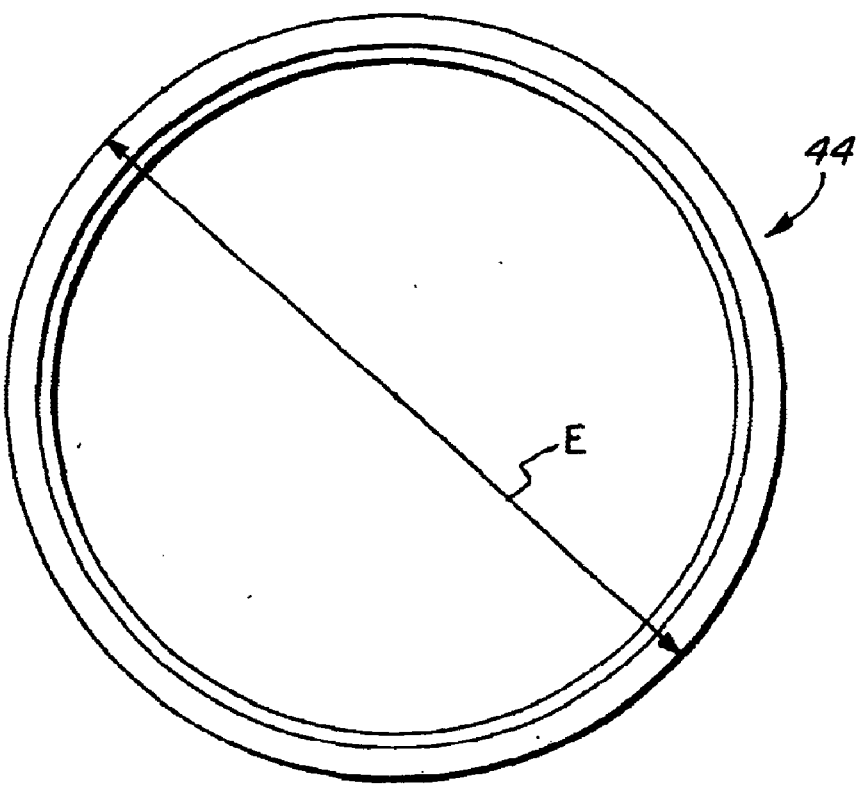
FIG. 9 is a top plan view of the upper housing member of FIG. 8.

Referring now to FIGS. 8 and 9 in addition to FIG. 4, upper housing member 44 is shown in more detail. Upper housing member 44 includes a generally horizontal member 80 which, when housing 12 is fully assembled as described more fully below, acts as an uppermost partition for housing 12. A wall 82 extends upwardly from an upper surface 84 of horizontal member 80 about a periphery thereof. Wall 82 defines a material holding chamber 86.

On the inside surface of the wall 82, toward the upper end thereof, there is a larger diameter portion terminating in a shoulder 38 which is arranged to receive and support a cover (not shown). The material to be tested is supported upon horizontal member 80 and enclosed within material holding chamber 86 by the cover (not shown).

Upper housing member 44 has an outer diameter E, at least toward the bottom portion thereof, which is dimensioned so as to be generally equal to, or slightly larger than, the diameter B of the second recess 64 defined by wall 52 of intermediate housing member 46. This is desirable so that when housing 12 is fully assembled as described more fully below, there is little or no relative play, and preferably a frictional fit, between upper housing member 44 and intermediate housing member 46.

Figure 10:
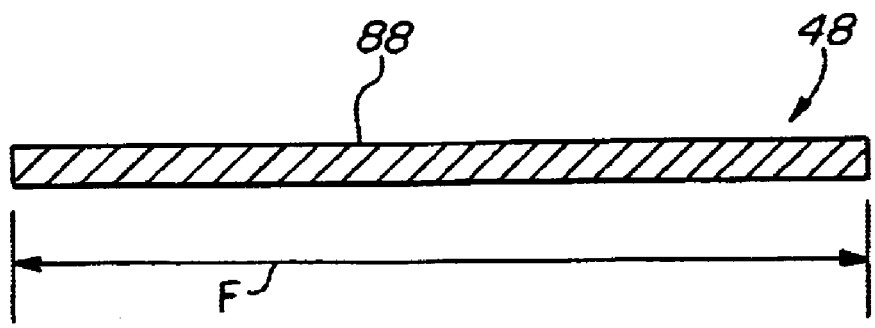
FIG. 10 is a partially cross-sectional side view of a lower housing member of the holder for materials used in measuring instruments of FIG. 1.
Figure 11:
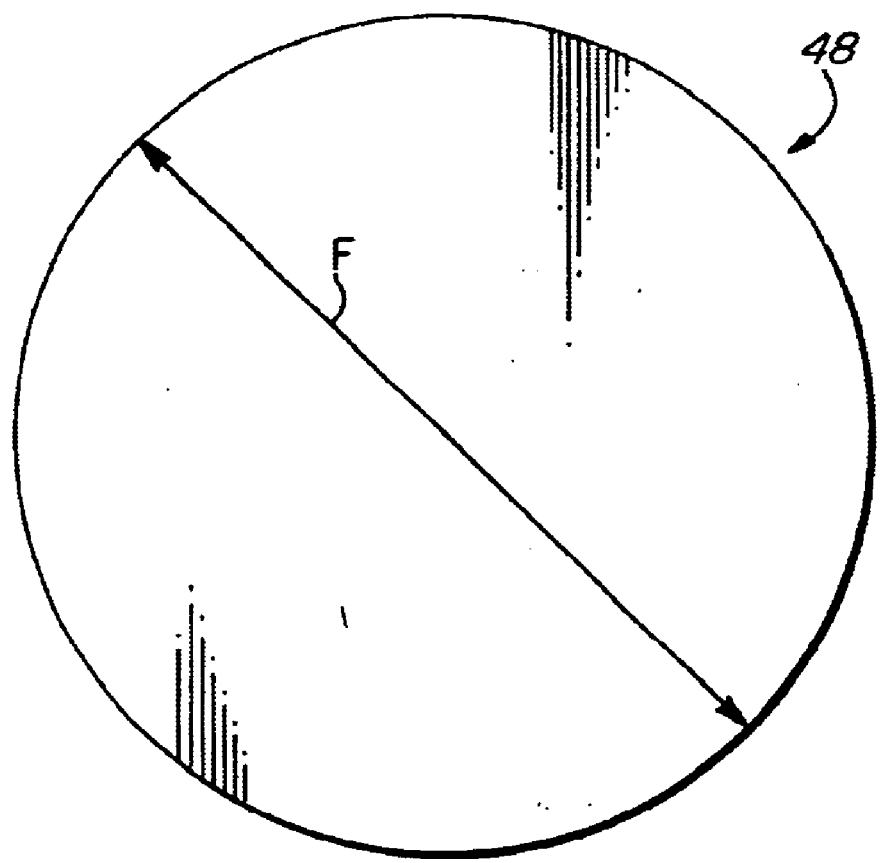
FIG. 11 is a top plan view of the lower housing member of FIG. 10.

Referring now to FIGS. 10 and 11 in addition to FIG. 4, lower housing member 48 is shown in more detail. Lower housing member 48 generally comprises a generally horizontal member 88 which, when housing 12 is fully assembled as described more fully below, acts as a lowermost partition for housing 12.

Lower housing member 48 has an outer diameter F, at least toward the top portion thereof, which is dimensioned so as to be generally equal to, or slightly larger than, the diameter D of the second recess 78 defined by wall 66 of intermediate housing member 46. This is desirable so that when housing 12 is fully assembled as described more fully below, there is little or no relative play, and preferably a frictional fit, between lower housing member 48 and intermediate housing member 46.

The assembly of material holder 10 is now described. Winding assembly 18 is disposed in first recess 62 defined by wall 52 of intermediate housing member 46 such that lead-out connector ribbons 22, 24 emerge through oppositely arranged slots 30, 32. The lower portion of upper housing member 44 is then press-fit into the second recess 64 defined by wall 52 of intermediate housing member 46. Because upper housing member 44 has an outer diameter E, at least toward the bottom portion thereof, which is dimensioned so as to be generally equal to, or slightly larger than, the diameter B of the second recess 64 defined by wall 52 of intermediate housing member 46, there is little or no relative play, and preferably a frictional fit, between upper housing member 44 and intermediate housing member 46. The second recess 64 defined by wall 52 of intermediate housing member 46 preferably has a beveled top edge 90 (best seen in FIG. 6) so as to facilitate insertion of upper housing member 44 therein.

The diameter A of first recess 62 defined by wall 52 of intermediate housing member 46 is selected such that winding assembly 18 fits therein. Moreover, the depth G of first recess 62 defined by wall 52 of intermediate housing member 46 is selected such that winding assembly 18 fits therein, and is preferably held snugly in the first cavity 14 defined between horizontal member 50 of intermediate housing member 46 and horizontal member 80 of upper housing member 44. The depth H of second recess 64 defined by wall 52 of intermediate housing member 46 is selected to be deep enough that the frictional fit of upper housing member 44 therein is maintained while material holder 10 is being assembled, but is not so deep that an excessive force is required to seat upper housing member 44 therein.

Winding assembly 20 is disposed in first recess 76 defined by wall 66 of intermediate housing member 46 such that lead-out connector ribbons 26, 28 emerge through oppositely arranged slots 34, 36. At least the upper portion of lower housing member 48 is then press-fit into the second recess 78 defined by wall 66 of intermediate housing member 46. Because lower housing member 48 has an outer diameter F, at least toward the top portion thereof, which is dimensioned so as to be generally equal to, or slightly larger than, the diameter D of the second recess 78 defined by wall 66 of intermediate housing member 46, there is little or no relative play, and preferably a frictional fit, between lower housing member 48 and intermediate housing member 46. The second recess 78 defined by wall 66 of intermediate housing member 46 preferably has a beveled lower edge 92 (best seen in FIG. 6) so as to facilitate insertion of lower housing member 48 therein.

The diameter C of first recess 76 defined by wall 66 of intermediate housing member 46 is selected such that winding assembly 20 fits therein. Moreover, the depth I of first recess 76 defined by wall 66 of intermediate housing member 46 is selected such that winding assembly 20 fits therein, and is preferably held snugly in the second cavity 16 defined between horizontal member 50 of intermediate housing member 46 and horizontal member 88 of lower housing member 48. The depth J of second recess 78 defined by wall 66 of intermediate housing member 46 is selected to be deep enough that the frictional fit of lower housing member 48 therein is maintained while material holder 10 is being assembled, but is not so deep that an excessive force is required to seat lower housing member 48 therein.

An electron beam welder is then applied to weld the various portions of housing 12, namely upper housing member 44, intermediate housing member 46 and lower housing member 48 together.

The present invention, therefore, provides a holder for materials used in measuring instruments and a fabrication method therefor which requires less labor intensive processes than are currently employed, which ensures proper spacing without requiring the use of precision tooling fixtures and pins, which allows for the spacing of the heater and the sensor to be accurately controlled, which facilitates reproducibility and consistent performance characteristics between material holders, which has a reduced number of parts, which has a reduced scrap rate, and which facilitates the accurate placement of the electron beam weld so as to inhibit spluttered platinum in the open cavities.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A holder for materials for use in a measuring instrument, said holder comprising:
   an intermediate housing member comprising:
      a generally horizontal member;
      an upper wall extending upwardly from an upper surface of the generally horizontal member, the upper wall defining a first recess adjacent the upper surface having a first diameter and a second recess adjacent the first recess having a second diameter, the second diameter being greater than the first diameter; and
      a lower wall extending downwardly from a lower surface of the generally horizontal member, the lower wall defining a third recess adjacent the lower surface having a third diameter and a fourth recess adjacent the third recess having a fourth diameter, the fourth diameter being greater than the third diameter;
   an upper housing member comprising a generally horizontal member and a wall extending upwardly from an upper surface of the generally horizontal member, the wall defining a material holding chamber, the upper housing member being seated within the second recess of the intermediate housing member;
   a lower housing member comprising a generally horizontal member, the lower housing member being seated within the fourth recess of the intermediate housing member;
   a first winding assembly disposed within a first cavity defined by the first recess, the generally horizontal member of the intermediate housing member and the generally horizontal member of the upper housing member; and
   a second winding assembly disposed within a second cavity defined by the third recess, the generally horizontal member of the intermediate housing member and the generally horizontal member of the lower housing member.

2. The holder of claim 1 wherein the upper housing member has an outer diameter which is generally equal to or slightly larger than the second diameter of the second recess so as to create a frictional fit between the intermediate housing member and the upper housing member.

3. The holder of claim 1 wherein the lower housing member has an outer diameter which is generally equal to or slightly larger than the fourth diameter of the fourth recess so as to create a frictional fit between the intermediate housing member and the lower housing member.

4. The holder of claim 1 wherein the intermediate housing member and the upper housing member are electron-beam welded together and wherein the intermediate housing member and the lower housing member are electron-beam welded together.

5. The holder of claim 1 wherein the first winding assembly comprises a pair of oppositely arranged lead-out connector ribbons and wherein the upper wall of the intermediate housing member includes a pair of oppositely arranged slots to allow the lead-out connector ribbons to emerge therethrough.

6. The holder of claim 1 wherein the second winding assembly comprises a pair of oppositely arranged lead-out connector ribbons and wherein the lower wall of the intermediate housing member includes a pair of oppositely arranged slots to allow the lead-out connector ribbons to emerge therethrough.

7. The holder of claim 1 wherein the second recess of the intermediate housing member has a beveled upper edge so as to facilitate insertion of the upper housing member therein.

8. The holder of claim 1 wherein the fourth recess of the intermediate housing member has a beveled lower edge so as to facilitate insertion of the lower housing member therein.

9. The holder of claim 1 wherein an inner surface of the wall of the upper housing member includes a shoulder therein which is arranged to receive and support a cover.

10. The holder of claim 1 wherein the upper housing member, the intermediate housing member and the lower housing member are formed from an alloy comprising about 80% platinum and about 20% iridium.

11. The holder of claim 1 wherein one of the first winding or the second winding comprises a heating winding and the other of the first winding or the second winding comprises a heat-sensing winding.

12. The holder of claim 1 further comprising a center post and a washer member attached to the lower housing member.

13. A housing for a material holder, said housing comprising:
   an intermediate housing member comprising a generally horizontal member, an upper recess and a lower recess;
   an upper housing member comprising a generally horizontal member and a wall defining a material holding chamber, the upper housing member being seated within the upper recess of the intermediate housing member;
   a lower housing member comprising a generally horizontal member, the lower housing member being seated within the lower recess of the intermediate housing member;
   wherein the upper recess, the generally horizontal member of the intermediate housing member and the generally horizontal member of the upper housing member define a first cavity adapted to receive a first winding assembly; and
   wherein the lower recess, the generally horizontal member of the intermediate housing member and the generally horizontal member of the lower housing member define a second cavity adapted to receive a second winding assembly.

14. The housing of claim 13 wherein the upper housing member has an outer diameter which is generally equal to or slightly larger than a diameter of a portion of the upper recess so as to create a frictional fit between the intermediate housing member and the upper housing member.

15. The housing of claim 13 wherein the lower housing member has an outer diameter which is generally equal to or slightly larger than a diameter of a portion of the lower recess so as to create a frictional fit between the intermediate housing member and the lower housing member.

16. The housing of claim 13 wherein the intermediate housing member and the upper housing member are electron-beam welded together and wherein the intermediate housing member and the lower housing member are electron-beam welded together.

17. The housing of claim 13 wherein the upper recess of the intermediate housing member has a beveled upper edge so as to facilitate insertion of the upper housing member therein.

18. The housing of claim 13 wherein the lower recess of the intermediate housing member has a beveled lower edge so as to facilitate insertion of the lower housing member therein.

19. The housing of claim 13 wherein an inner surface of the wall of the upper housing member includes a shoulder therein which is adapted to receive and support a cover.

20. The housing of claim 13 wherein the upper housing member, the intermediate housing member and the lower housing member are formed from an alloy comprising about 80% platinum and about 20% iridium.

21. A method for fabricating a holder for materials for use in a measuring instrument, said method comprising the steps of:
providing an intermediate housing member comprising a generally horizontal member, an upper recess and a lower recess;
disposing a first winding assembly within the upper recess;
seating an upper housing member comprising a generally horizontal member and a wall defining a material holding chamber within the upper recess in order to define, with the upper recess, the generally horizontal member of the intermediate housing member and the generally horizontal member of the upper housing member, a first cavity with the first winding housed therein;
disposing a second winding assembly within the lower recess;
seating a lower housing member comprising a generally horizontal member within the lower recess in order to define, with the lower recess, the generally horizontal member of the intermediate housing member and the generally horizontal member of the lower housing member, a second cavity with the second winding housed therein.

22. The method of claim 21 further comprising the steps of:
electron beam welding the intermediate housing member and the upper housing member together; and
electron beam welding the intermediate housing member and the lower housing member together.

23. The holder of claim 22 further comprising the step of creating a bevel in an upper edge of the upper recess of the intermediate housing member has so as to facilitate insertion of the upper housing member therein.

24. The holder of claim 22 further comprising the step of creating a bevel in a lower edge of the lower recess of the intermediate housing member has so as to facilitate insertion of the lower housing member therein.

25. The holder of claim 22 further comprising the step of creating a shoulder in an inner surface of the wall of the upper housing member, which shoulder is adapted to receive and support a cover.

26. A holder for materials for use in a measuring instrument, said holder comprising:
a three-piece housing consisting of an upper housing member, an intermediate housing member and a lower housing member, wherein the intermediate housing member and the upper housing member are electron-beam welded together and wherein the intermediate housing member and the lower housing member are electron-beam welded together, the three-piece housing defining a first cavity and a second cavity;
a first winding assembly disposed within the first cavity; and
a second winding assembly disposed within the second cavity.

* * * * *